United States Patent [19]

Takahara

[11] Patent Number: 4,473,691

[45] Date of Patent: Sep. 25, 1984

[54] PROCESS FOR PREPARING 5-FLUOROCYTOSINE SALT

[75] Inventor: Takao Takahara, Osaka, Japan

[73] Assignee: Daikin Kogyo Co., Ltd., Osaka, Japan

[21] Appl. No.: 368,204

[22] Filed: Apr. 14, 1982

[30] Foreign Application Priority Data

Apr. 14, 1981 [JP] Japan ................... 56-56620

[51] Int. Cl.³ .......................... C07D 239/47
[52] U.S. Cl. ................................. 544/317
[58] Field of Search ........................ 544/317

[56] References Cited

U.S. PATENT DOCUMENTS 3,682,917  8/1972  Knuniants et al. ............... 544/313
4,029,661  6/1977  Schuman et al. ................. 544/313
4,122,251  10/1978  Misaki et al. .................... 544/313

FOREIGN PATENT DOCUMENTS 154171  9/1982  Japan .

Primary Examiner—Paul M. Coughlan, Jr.
Attorney, Agent, or Firm—Birch, Stewart, Kolasch & Birch

[57] ABSTRACT

5-Fluorocytosine hydrofluoride of high purity is prepared by fluorinating cytosine with fluorine gas in the presence of hydrogen fluoride, followed by treatment of the resultant fluorinated product in the reaction mixture at a temperature higher than the fluorination temperature.

9 Claims, No Drawings

PROCESS FOR PREPARING 5-FLUOROCYTOSINE SALT

The present invention relates to a process for preparing 5-fluorocytosine salt. More particularly, it relates to an improved process for preparing 5-fluorocytosine hydrofluoride by direct fluorination of cytosine or its hydrofluoride with fluorine gas in the presence of hydrogen fluoride.

5-Fluorocytosine hydrofluoride is known to be an intermediate for the production of 5-fluorocytosine of the formula:

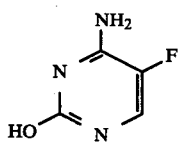

which is useful as an antibacterial agent.

There is known a process for preparing 5-fluorocytosine by direct fluorination of cytosine with fluorine gas (cf. Japanese Patent Publication No. 37553/1979). This process comprises fluorination of cytosine, followed by treatment of the resultant intermediate with an amine to obtain 5-fluorocytosine. The conversion in this process is presumed to proceed as follows:

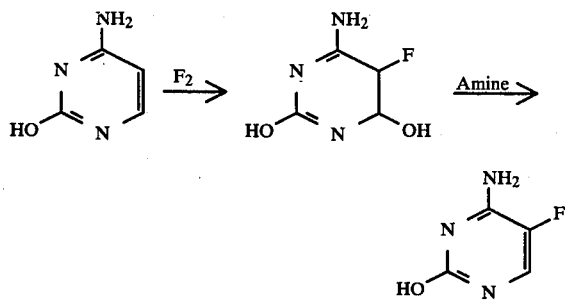

Although the above process has some advantages over other known processes, it still has a disadvantage that during the latter step for treatment of the intermediate with an amine, the amino group at the 4-position tends to be eliminated so that not only the purity but also the yield of the desired 5-fluorocytosine are lowered.

As a result of an extensive study, it has been found that when cytosine is fluorinated with fluorine gas in the presence of hydrogen fluoride and the resultant fluorinated product in the reaction mixture is treated at a temperature higher than the fluorination temperature, no elimination of the amino group at the 4-position takes place, and the desired 5-fluorocytosine is obtained in a good yield with a high purity.

The present invention is based on this finding and provides a process for preparing 5-fluorocytosine hydrofluoride which comprising fluorinating cytosine or its hydrofluoride with fluorine gas in the presence of hydrogen fluoride, followed by treatment of the resultant fluorinated product in the reaction mixture at a temperature higher than the fluorination temperature.

The conversion in the process of this invention is presumed as follows:

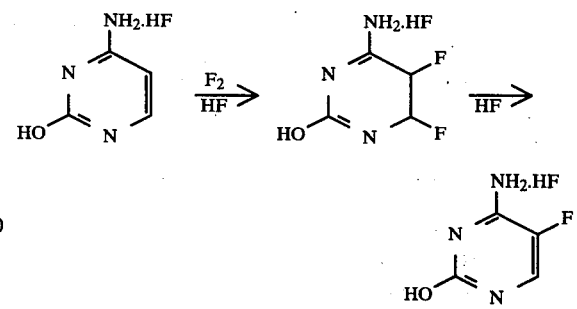

The fluorination may be carried out in the presence of hydrogen fluoride, when desired, in an inert solvent. Specific examples of the solvent are halogenated hydrocarbons such as chlorohydrocarbons (e.g. chloroform, carbon tetrachloride), chlorofluorohydrocarbons (e.g. trichlorotrifluoroethane) and perfluorohydrocarbons (e.g. perfluorodekalin), ketones (e.g. hexafluoroacetone), organic acids (e.g. acetic acid, trifluoroacetic acid, polyfluoropropionic acid) and alcohols (e.g. ethanol, trifluoroethanol). The solvent may be admixed with hydrogen fluoride in such an amount that the former does not adversely affect the fluorination.

Theoretically, the molar ratio of hydrogen fluoride to cytosine may be 1:1 or more, preferably 2:1 or more. Practically, in order to dissolve cytosine sufficiently, an excess amount of hydrogen fluoride is used or the solvent is used.

The molar ratio of the fluorine gas to cytosine or its hydrofluoride may be from 1:1 to 2:1. The fluorine gas is preferably diluted with an inert gas (e.g. nitrogen) in order to avoid a rapid reaction. When undiluted fluorine gas is used, it is preferred to employ hydrogen fluoride or a nonflammable halogenated solvent as the reaction medium.

The reaction in the former step for fluorination of cytosine or its hydrofluoride may be carried out at a temperature not higher than 0° C. but not lower than the freezing point of the reaction medium. The reaction in the latter step for dehydrofluorination of the fluorinated product may be carried out at a temperature higher than the fluorination temperature in the former step, preferably of from 5° C. to 20° C.

After the reaction in the latter step is completed, hydrogen fluoride is removed from the reaction mixture at room temperature under atmospheric or reduced pressure, and the residue is extracted with a solvent such as water or methanol. The extract is, then, evaporated under reduced pressure to obtain 5-fluorocytosine hydrofluoride.

5-Fluorocytosine hydrofluoride may be deacidified and converted into 5-fluorocytosine by a conventional method, for example, by treating the former with a base such as ammonia or calcium hydroxide.

The present invention will be hereinafter explained further in detail by the following Example.

EXAMPLE

Into a bottomed tube (inner diameter, 1 cm) made of polychlorotrifluoroethylene resin (Trade Name "Daiflon", Daikin Kogyo Co., Ltd.), cytosine (0.444 g, 4 mmol) and anhydrous hydrogen fluoride (10 g) were charged at −50° C. Then, the temperature was raised to −5° C., and fluorine gas (0.228 g, 6 mmol) diluted with the same volume of nitrogen gas bubbled therein for one hour. After fluorination was completed, the temperature of the tube was elevated up to room temperature, and hydrogen fluoride was evaporated thoroughly under reduced pressure.

Methanol (50 ml) was added thereto, and the resulting mixture was evaporated at room temperature under reduced pressure. The residue was recrystallized from methanol to give 5-fluorocytosine hydrofluoride (0.533 g). M.P. 136° C.

$^1$H-NMR(DMSO), $\delta_{H6}=7.83$ ppm.

$^{19}$F-NMR(DMSO), $\delta_{F5}=91.3$ ppm.

What is claimed is:

1. A process for preparing 5-fluorocytosine hydrofluoride which comprises fluorinating cytosine or the hydrofluoride thereof with fluorine gas in the presence of anhydrous hydrogen fluoride and then elevating the temperature of the reaction mixture containing the resultant fluorinated product to a temperature higher than the temperature of fluorination.

2. The process according to claim 1, wherein the fluorination is carried out in an inert solvent.

3. The process according to claim 2, wherein the inert solvent is selected from the group consisting of halogenated hydrocarbons, ketones, organic acids and alcohols.

4. The process according to claim 1, wherein the fluorine gas is diluted with an inert gas.

5. The process according to claim 1, wherein the fluorination is effected at a temperature not higher than 0° C.

6. The process according to claim 1, wherein the fluorination is conducted at a temperature not higher than 0° C. and the temperature of the reaction mixture is then elevated to 5° to 20° C.

7. A process for preparing 5-fluorocytosine hydrofluoride which comprises fluorinating cytosine or the hydrofluoride thereof with fluorine gas in the presence of anhydrous hydrogen fluoride at a temperature not higher than 0° C., elevating the temperature of the reaction mixture containing the resultant fluorinated product to a temperature of 5° to 20° C., and separating the 5-fluorocytosine hydrofluoride from the reaction mixture.

8. The process according to claim 7, wherein the fluorination is carried out in an anhydrous inert solvent.

9. The process according to claim 7, wherein the fluorine gas is diluted with an inert gas.

* * * * *